(12) United States Patent
Strul et al.

(10) Patent No.: US 8,551,082 B2
(45) Date of Patent: *Oct. 8, 2013

(54) RADIO-FREQUENCY GENERATOR FOR POWERING AN ABLATION DEVICE

(75) Inventors: Bruno Strul, Portolla Valley, CA (US); Csaba Truckai, Sunnyvale, CA (US); Russel M. Sampson, Mountain View, CA (US); Mark L. Kane, Cupertino, CA (US)

(73) Assignee: Cytyc Surgical Products, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/423,908

(22) Filed: Mar. 19, 2012

(65) Prior Publication Data

US 2012/0179155 A1    Jul. 12, 2012

Related U.S. Application Data

(60) Continuation of application No. 12/775,752, filed on May 7, 2010, now abandoned, which is a division of application No. 11/211,016, filed on Aug. 24, 2005, now Pat. No. 7,717,909, which is a division of application No. 10/328,447, filed on Dec. 23, 2002, now Pat. No. 7,074,217, which is a division of application No. 09/306,480, filed on May 6, 1999, now Pat. No. 6,508,815.

(60) Provisional application No. 60/084,712, filed on May 8, 1998.

(51) Int. Cl.
    *A61B 18/12*    (2006.01)
(52) U.S. Cl.
    USPC .............................................. 606/32; 606/34

(58) Field of Classification Search
    USPC ................... 606/27–38, 41; 607/96, 98, 105, 607/113, 115
    See application file for complete search history.

(56) References Cited

U.S. PATENT DOCUMENTS

| 552,832 A | 1/1896 | Fort |
| 725,731 A | 4/1903 | Linn |

(Continued)

FOREIGN PATENT DOCUMENTS

| DE | 384246 | 10/1923 |
| DE | 22 22 820 | 11/1973 |

(Continued)

OTHER PUBLICATIONS

"Essure, Permanent Birth Control by Conceptus: What is Essure?" Product Information Sheet [on-line] [retrieved Oct. 19, 2004] Retrieved from the Internet: <URL: http://www.essure.com/consumer/c.sub.--what.sub.--is.sub.--essure.aspx>.

(Continued)

*Primary Examiner* — Aaron Roane
(74) *Attorney, Agent, or Firm* — Robert P. Smith

(57) ABSTRACT

An apparatus and method for use in performing ablation of organs and other tissues includes a radio frequency generator which provides a radio frequency signal to ablation electrodes. The power level of the radio frequency signal is determined based on the subject area of ablation. The radio frequency signal is coupled with the ablation electrodes through a transformation circuit. The transformation circuit includes a high impedance transformation circuit and a low impedance transformation circuit. The high or low impedance transformation circuit is selected based on the impedance of the ablation electrodes in contact with the subject tissue. Vacuum level, impedance level, resistance level, and time are measured during ablation. If these parameters exceed determinable limits the ablation procedure is terminated.

19 Claims, 9 Drawing Sheets

(56) References Cited

U.S. PATENT DOCUMENTS

| | | | |
|---|---|---|---|
| 1,620,929 | A | 3/1927 | Wallerich |
| 1,827,306 | A | 10/1931 | Chapman et al. |
| 2,190,383 | A | 2/1940 | Newman |
| 2,347,195 | A | 4/1944 | Huff |
| 2,466,042 | A | 4/1949 | Reich et al. |
| 3,228,398 | A | 1/1966 | Leonard et al. |
| 3,324,855 | A | 6/1967 | Heimlich |
| 3,645,265 | A | 2/1972 | Majzlin |
| 3,840,016 | A | 10/1974 | Lindemann |
| 3,845,771 | A | 11/1974 | Vise |
| 3,858,586 | A | 1/1975 | Lessen |
| 3,877,464 | A | 4/1975 | Vermes |
| 3,924,628 | A | 12/1975 | Droegemueller et al. |
| 3,948,270 | A | 4/1976 | Hasson |
| 3,967,625 | A | 7/1976 | Yoon |
| 3,971,378 | A | 7/1976 | Krantz |
| 4,022,215 | A | 5/1977 | Benson |
| 4,057,063 | A | 11/1977 | Gieles et al. |
| 4,082,096 | A | 4/1978 | Benson |
| 4,094,320 | A | 6/1978 | Newton et al. |
| 4,158,050 | A | 6/1979 | Zipper |
| 4,185,618 | A | 1/1980 | Corey |
| 4,233,025 | A | 11/1980 | Larson et al. |
| 4,347,842 | A | 9/1982 | Beale |
| 4,359,454 | A | 11/1982 | Hoffman |
| 4,380,238 | A | 4/1983 | Colucci et al. |
| 4,415,288 | A | 11/1983 | Gordon et al. |
| 4,449,528 | A | 5/1984 | Auth et al. |
| 4,465,072 | A | 8/1984 | Taheri |
| 4,492,231 | A | 1/1985 | Auth |
| 4,532,483 | A | 7/1985 | Schminke |
| 4,532,924 | A | 8/1985 | Auth et al. |
| 4,568,326 | A | 2/1986 | Rangaswamy |
| 4,582,057 | A | 4/1986 | Auth et al. |
| 4,601,698 | A | 7/1986 | Moulding, Jr. |
| 4,606,336 | A | 8/1986 | Zeluff |
| 4,628,924 | A | 12/1986 | Cimber |
| 4,662,383 | A | 5/1987 | Sogawa et al. |
| 4,676,258 | A | 6/1987 | Inokuchi et al. |
| 4,691,703 | A | 9/1987 | Auth et al. |
| 4,700,701 | A | 10/1987 | Montaldi |
| 4,739,759 | A | 4/1988 | Rexroth et al. |
| 4,765,331 | A | 8/1988 | Petruzzi et al. |
| 4,788,966 | A | 12/1988 | Yoon |
| 4,807,620 | A | 2/1989 | Strul et al. |
| 4,832,048 | A | 5/1989 | Cohen |
| 4,865,047 | A | 9/1989 | Chou et al. |
| 4,869,268 | A | 9/1989 | Yoon |
| 4,946,440 | A | 8/1990 | Hall |
| 4,949,718 | A | 8/1990 | Neuwirth et al. |
| 4,955,377 | A | 9/1990 | Lennox et al. |
| 4,960,133 | A | 10/1990 | Hewson |
| 4,961,435 | A | 10/1990 | Kitagawa et al. |
| 4,979,948 | A | 12/1990 | Geddes et al. |
| 4,981,465 | A | 1/1991 | Ballan et al. |
| 4,983,177 | A | 1/1991 | Wolf |
| 5,026,379 | A | 6/1991 | Yoon |
| 5,047,028 | A | 9/1991 | Qian |
| 5,057,106 | A | 10/1991 | Kasevich et al. |
| 5,065,751 | A | 11/1991 | Wolf |
| 5,078,717 | A | 1/1992 | Parins et al. |
| 5,084,044 | A | 1/1992 | Quint |
| 5,105,808 | A | 4/1992 | Neuwirth et al. |
| 5,147,353 | A | 9/1992 | Everett |
| 5,159,925 | A | 11/1992 | Neuwirth et al. |
| 5,160,334 | A | 11/1992 | Billings et al. |
| 5,178,148 | A * | 1/1993 | Lacoste et al. ................ 600/439 |
| 5,186,181 | A | 2/1993 | Franconi et al. |
| 5,188,122 | A | 2/1993 | Phipps et al. |
| 5,188,602 | A | 2/1993 | Nichols |
| 5,217,473 | A | 6/1993 | Yoon |
| 5,226,908 | A | 7/1993 | Yoon |
| 5,242,437 | A | 9/1993 | Everett et al. |
| 5,248,312 | A | 9/1993 | Langberg |
| 5,263,585 | A | 11/1993 | Lawhon et al. |
| 5,277,201 | A | 1/1994 | Stern |
| 5,308,327 | A | 5/1994 | Heaven et al. |
| 5,318,532 | A | 6/1994 | Frassica |
| 5,322,507 | A | 6/1994 | Costello et al. |
| 5,334,193 | A | 8/1994 | Nardella |
| 5,334,209 | A | 8/1994 | Yoon |
| 5,354,295 | A | 10/1994 | Guglielmi et al. |
| 5,357,956 | A | 10/1994 | Nardella |
| 5,364,393 | A | 11/1994 | Auth et al. |
| 5,370,649 | A | 12/1994 | Gardetto et al. |
| 5,374,261 | A | 12/1994 | Yoon |
| 5,374,283 | A | 12/1994 | Flick |
| 5,380,317 | A | 1/1995 | Everett et al. |
| 5,383,917 | A | 1/1995 | Desai et al. |
| 5,385,544 | A | 1/1995 | Edwards et al. |
| 5,395,311 | A | 3/1995 | Andrews |
| 5,405,322 | A | 4/1995 | Lennox et al. |
| 5,407,071 | A | 4/1995 | Lawhon et al. |
| 5,423,808 | A | 6/1995 | Edwards et al. |
| 5,433,708 | A | 7/1995 | Nichols et al. |
| 5,437,629 | A | 8/1995 | Goldrath |
| 5,443,470 | A | 8/1995 | Stern et al. |
| 5,451,204 | A | 9/1995 | Yoon |
| 5,474,089 | A | 12/1995 | Waynant |
| 5,484,400 | A | 1/1996 | Edwards et al. |
| 5,498,261 | A | 3/1996 | Strul |
| 5,505,730 | A | 4/1996 | Edwards |
| 5,507,743 | A | 4/1996 | Edwards et al. |
| 5,514,091 | A | 5/1996 | Yoon |
| 5,540,655 | A | 7/1996 | Edwards et al. |
| 5,540,681 | A | 7/1996 | Strul et al. |
| 5,542,916 | A | 8/1996 | Hirsch et al. |
| 5,558,672 | A | 9/1996 | Edwards et al. |
| 5,562,703 | A | 10/1996 | Desai |
| 5,562,720 | A | 10/1996 | Stern et al. |
| 5,573,533 | A | 11/1996 | Strul |
| 5,575,788 | A | 11/1996 | Baker et al. |
| 5,588,961 | A | 12/1996 | Leone et al. |
| 5,593,404 | A | 1/1997 | Costello et al. |
| 5,599,345 | A | 2/1997 | Edwards et al. |
| 5,599,346 | A | 2/1997 | Edwards et al. |
| 5,609,598 | A | 3/1997 | Laufer et al. |
| 5,613,950 | A | 3/1997 | Yoon |
| 5,620,481 | A | 4/1997 | Desai et al. |
| 5,649,924 | A | 7/1997 | Everett et al. |
| 5,656,013 | A | 8/1997 | Yoon |
| 5,658,316 | A | 8/1997 | Lamond et al. |
| 5,667,520 | A | 9/1997 | Bonutti |
| 5,697,882 | A | 12/1997 | Eggers et al. |
| 5,702,438 | A | 12/1997 | Avitall |
| 5,716,343 | A | 2/1998 | Kriesel et al. |
| 5,722,975 | A | 3/1998 | Edwards et al. |
| 5,730,136 | A | 3/1998 | Laufer et al. |
| 5,730,725 | A | 3/1998 | Yoon |
| 5,733,252 | A | 3/1998 | Yoon |
| 5,769,880 | A | 6/1998 | Truckai et al. |
| 5,779,698 | A | 7/1998 | Clayman et al. |
| 5,797,903 | A | 8/1998 | Swanson et al. |
| 5,800,482 | A | 9/1998 | Pomeranz et al. |
| 5,807,389 | A | 9/1998 | Gardetto et al. |
| 5,810,847 | A | 9/1998 | Laufer et al. |
| 5,827,273 | A | 10/1998 | Edwards |
| 5,843,026 | A | 12/1998 | Edwards et al. |
| 5,843,121 | A | 12/1998 | Yoon |
| 5,846,238 | A | 12/1998 | Jackson et al. |
| 5,865,788 | A | 2/1999 | Edwards et al. |
| 5,871,469 | A | 2/1999 | Eggers et al. |
| 5,879,348 | A | 3/1999 | Owens et al. |
| 5,885,601 | A | 3/1999 | Sokal |
| 5,888,198 | A | 3/1999 | Eggers et al. |
| 5,891,134 | A | 4/1999 | Goble et al. |
| 5,891,136 | A | 4/1999 | McGee et al. |
| 5,897,551 | A | 4/1999 | Everett et al. |
| 5,897,553 | A | 4/1999 | Mulier et al. |
| 5,935,123 | A | 8/1999 | Edwards et al. |
| 5,935,137 | A | 8/1999 | Saadat et al. |
| 5,938,660 | A | 8/1999 | Swartz et al. |
| 5,944,715 | A | 8/1999 | Goble et al. |
| 5,954,717 | A | 9/1999 | Behl et al. |

| | | |
|---|---|---|
| 5,979,446 A | 11/1999 | Loy |
| 5,997,534 A | 12/1999 | Tu et al. |
| 6,002,968 A | 12/1999 | Edwards |
| 6,014,589 A | 1/2000 | Farley et al. |
| 6,033,397 A | 3/2000 | Laufer et al. |
| 6,036,687 A | 3/2000 | Laufer et al. |
| 6,041,260 A | 3/2000 | Stern et al. |
| 6,042,596 A | 3/2000 | Bonutti |
| 6,047,700 A | 4/2000 | Eggers et al. |
| 6,066,139 A | 5/2000 | Ryan et al. |
| 6,068,613 A | 5/2000 | Kriesel et al. |
| 6,068,626 A | 5/2000 | Harrington et al. |
| 6,071,277 A | 6/2000 | Farley et al. |
| 6,074,386 A | 6/2000 | Goble et al. |
| 6,077,257 A | 6/2000 | Edwards et al. |
| 6,096,052 A | 8/2000 | Callister et al. |
| 6,112,123 A | 8/2000 | Kelleher et al. |
| 6,117,101 A | 9/2000 | Diederich et al. |
| 6,123,702 A | 9/2000 | Swanson et al. |
| 6,135,997 A | 10/2000 | Laufer et al. |
| 6,139,527 A | 10/2000 | Laufer et al. |
| 6,139,546 A | 10/2000 | Koenig et al. |
| 6,152,899 A | 11/2000 | Farley et al. |
| 6,159,207 A | 12/2000 | Yoon |
| 6,164,280 A | 12/2000 | Everett et al. |
| 6,165,172 A | 12/2000 | Farley et al. |
| 6,179,832 B1 | 1/2001 | Jones et al. |
| 6,183,468 B1 | 2/2001 | Swanson et al. |
| 6,193,713 B1 | 2/2001 | Geistert et al. |
| 6,197,025 B1 | 3/2001 | Grossi et al. |
| 6,200,312 B1 | 3/2001 | Zikorus et al. |
| 6,231,496 B1 | 5/2001 | Wilk et al. |
| 6,231,507 B1 | 5/2001 | Zikorus et al. |
| 6,234,178 B1 | 5/2001 | Goble et al. |
| 6,237,606 B1 | 5/2001 | Zikorus et al. |
| 6,238,393 B1 | 5/2001 | Mulier et al. |
| 6,245,065 B1 | 6/2001 | Panescu et al. |
| 6,245,090 B1 | 6/2001 | Gilson et al. |
| 6,254,601 B1 | 7/2001 | Burbank et al. |
| 6,258,084 B1 | 7/2001 | Goldman et al. |
| 6,258,085 B1 | 7/2001 | Eggleston |
| 6,263,248 B1 | 7/2001 | Farley et al. |
| 6,277,089 B1 | 8/2001 | Yoon |
| 6,293,942 B1 | 9/2001 | Goble et al. |
| 6,296,639 B1 | 10/2001 | Truckai et al. |
| 6,309,384 B1 | 10/2001 | Harrington et al. |
| 6,315,776 B1 | 11/2001 | Edwards et al. |
| 6,322,559 B1 | 11/2001 | Daulton et al. |
| 6,346,102 B1 | 2/2002 | Harrington et al. |
| 6,352,549 B1 | 3/2002 | Everett |
| 6,364,877 B1 | 4/2002 | Goble et al. |
| 6,369,465 B1 | 4/2002 | Swanson |
| 6,395,012 B1 | 5/2002 | Yoon et al. |
| 6,398,780 B1 | 6/2002 | Farley et al. |
| 6,402,742 B1 * | 6/2002 | Blewett et al. ............... 606/34 |
| 6,428,537 B1 | 8/2002 | Swanson et al. |
| 6,432,116 B1 | 8/2002 | Callister et al. |
| 6,451,015 B1 | 9/2002 | Rittman, III et al. |
| 6,475,213 B1 | 11/2002 | Whayne et al. |
| 6,485,487 B1 | 11/2002 | Sherman |
| 6,485,500 B1 | 11/2002 | Kokish et al. |
| 6,490,474 B1 * | 12/2002 | Willis et al. ............... 600/424 |
| 6,508,815 B1 | 1/2003 | Strul et al. |
| 6,554,780 B1 | 4/2003 | Sampson et al. |
| 6,663,626 B2 | 12/2003 | Truckai et al. |
| 6,679,269 B2 | 1/2004 | Swanson |
| 6,712,810 B2 | 3/2004 | Harrington et al. |
| 6,712,815 B2 | 3/2004 | Sampson et al. |
| 6,726,682 B2 | 4/2004 | Harrington et al. |
| 6,743,184 B2 | 6/2004 | Sampson et al. |
| 6,764,488 B1 | 7/2004 | Burbank et al. |
| 6,813,520 B2 | 11/2004 | Sampson et al. |
| 6,964,274 B1 | 11/2005 | Ryan et al. |
| 7,074,217 B2 | 7/2006 | Strul et al. |
| 7,407,502 B2 | 8/2008 | Strul et al. |
| 7,512,445 B2 | 3/2009 | Truckai et al. |
| 7,604,633 B2 | 10/2009 | Truckai et al. |
| 7,717,909 B2 | 5/2010 | Strul et al. |
| 7,731,712 B2 | 6/2010 | Sampson et al. |
| 7,846,160 B2 | 12/2010 | Payne et al. |
| 2001/0041900 A1 | 11/2001 | Callister et al. |
| 2002/0022870 A1 | 2/2002 | Truckai et al. |
| 2002/0029051 A1 | 3/2002 | Callister et al. |
| 2002/0072499 A1 | 6/2002 | Clagett |
| 2002/0072745 A1 | 6/2002 | Truckai et al. |
| 2002/0177846 A1 | 11/2002 | Mulier et al. |
| 2003/0093101 A1 | 5/2003 | O'Heeron et al. |
| 2003/0130711 A1 | 7/2003 | Pearson et al. |
| 2003/0199863 A1 | 10/2003 | Swanson et al. |
| 2004/0054368 A1 | 3/2004 | Truckai et al. |
| 2004/0118166 A1 | 6/2004 | Huang et al. |
| 2004/0172051 A1 | 9/2004 | Ravikumar |
| 2004/0204720 A1 | 10/2004 | Harrington et al. |
| 2004/0255958 A1 | 12/2004 | Harrington et al. |
| 2005/0085880 A1 | 4/2005 | Truckai et al. |
| 2005/0155608 A1 | 7/2005 | Pavcnik et al. |
| 2005/0217680 A1 | 10/2005 | Callister et al. |
| 2006/0135956 A1 | 6/2006 | Sampson et al. |
| 2008/0071269 A1 | 3/2008 | Hilario et al. |
| 2010/0036372 A1 | 2/2010 | Truckai et al. |
| 2010/0217256 A1 | 8/2010 | Strul et al. |
| 2012/0179155 A1 | 7/2012 | Strul et al. |

FOREIGN PATENT DOCUMENTS

| | | |
|---|---|---|
| DE | 40 01 086 | 7/1991 |
| EP | 0 056 178 | 4/1981 |
| EP | 0 584 930 | 7/1993 |
| EP | 1 400 182 | 3/2004 |
| EP | 1 568 325 | 8/2005 |
| FR | 774 550 | 12/1934 |
| FR | 2 115 706 | 7/1972 |
| GB | 2 317 566 | 4/1998 |
| JP | 48-67586 | 12/1971 |
| JP | 58-32756 | 2/1983 |
| JP | 63-318934 | 12/1988 |
| WO | 92/19145 | 11/1992 |
| WO | 94/00178 | 1/1994 |
| WO | 94/07445 | 4/1994 |
| WO | 94/10948 | 5/1994 |
| WO | 94/23794 | 10/1994 |
| WO | 95/04385 | 2/1995 |
| WO | 95/05869 | 3/1995 |
| WO | 95/07664 | 3/1995 |
| WO | 95/10326 | 4/1995 |
| WO | 96/00042 | 1/1996 |
| WO | 97/12569 | 4/1997 |
| WO | 97/41785 | 11/1997 |
| WO | 98/38932 | 9/1998 |
| WO | 99/58070 | 11/1999 |
| WO | 01/97897 | 12/2001 |

OTHER PUBLICATIONS

"Essure: the non-incisional approach to permanent birth control", Patient Information Booklet, .COPYRGT. 2004 by Conceptus Incorporated.

"Tubal Ligation and Resection: Tubal Ligation by Parkland and Irving Methods" Datasheet [on-line] Chapel Hill Tubal Reversal Center, 2004 [retrieved on Oct. 19, 2004] Retrieved from the Internet: <URL:http://www.tubal-reversal.net/ print/printer-friendly-tubal.sub.--ligation-.sub.--resection.htm>.

"Tubal Ligation Methods: Coagulation Methods of Tubal Ligation" Datasheet [on-line] Chapel Hill Tubal Reversal Center, 2004, [retrieved Oct. 19, 2004] Retrieved from the Internet: <http://www.tubal-reversal.net/tubal.sub.--ligation. sub.--coagulation.htm>.

"Tubal Ligation—Fimbriectomy: Tubal Reversal is Possible after Fimbriectomy" Datasheet [on-line] Chapel Hill Tubal Reversal Center, 2004 [retrieved on Oct. 19, 2004] Retrieved from the Internet: <URL: http://www.tubal-reversal.net/ print/printer-friendly-tubal.sub.--ligation-.sub.--fimbriectomy.htm>.

"Tubal Ligation—Pomeroy Technique: Pomeroy Tubal Ligation and Resection" Datasheet [on-line] Chapel Hill Tubal Reversal Center, 2004 [retrieved Oct. 19, 2004 ] Retrieved from the Internet: <http://www.tubal-reversal.net/print/ printer-friendly-tubal.sub.--ligation-.sub.--Pomeroy.htm>.

"Tubal Ligation—Tubal Ring or Clip: Tubal Ligation with Tubal Rings or Tubal Clips" Datasheet [on-line] Chapel Hill Tubal Reversal Center, 2004 [retrieved Oct. 19, 2004] Retrieved from the Internet: <URL: http://www.tubal-reversal.net/tubal.sub.--ligation-tubal.sub.--ring-tubal-.sub.--clip.htm>.

Adiana options for women—how it works. (Dec. 31, 2005). Retrieved from http://web.archive.org/web/20051124001429/www.adiana.com/products.sub.--h- ow.php.

C. Nibley et al., "Prevention of Impedance Rise During Radiofrequency Current Catheter Ablation by Intra-Electrode Tip Chilling," Circulation [Abstracts From the 67th Scientific Sessions, Dallas Convention Center, Dallas, Texas, Nov. 14-17, 1994], vol. 90, No. 4, Part 2, Oct. 1994, p. 460.

D.E. Haines et al., "Observations on Electrode-Tissue Interface Temperature and Effect on Electrical Impedance During Radiofrequency Ablation of Ventricular Myocardium," Circulation, vol. 82, No. 3, Sep. 1990, pp. 1034-1038.

METI-MyriadLase, SteriLase, Powerpoint Presentation, published at least as of Jun. 13, 2006, 6 pages.

W.M. Jackman et al., "Radiofrequency Current Directed Across the Mitral Anulus With a Bipolar Epicardial-Endocardial Catheter Electrode Configuration in Dogs," Circulation, vol. 78, No. 5, Nov. 1988, pp. 1288-1298.

First Request for Ex Partes Reexamination of U.S. Patent No. 5,769,880, filed Jul. 27, 1999.

Second Request for Ex Partes Reexamination of U.S. Patent No. 5,769,880, filed Nov. 22, 2000.

\* cited by examiner

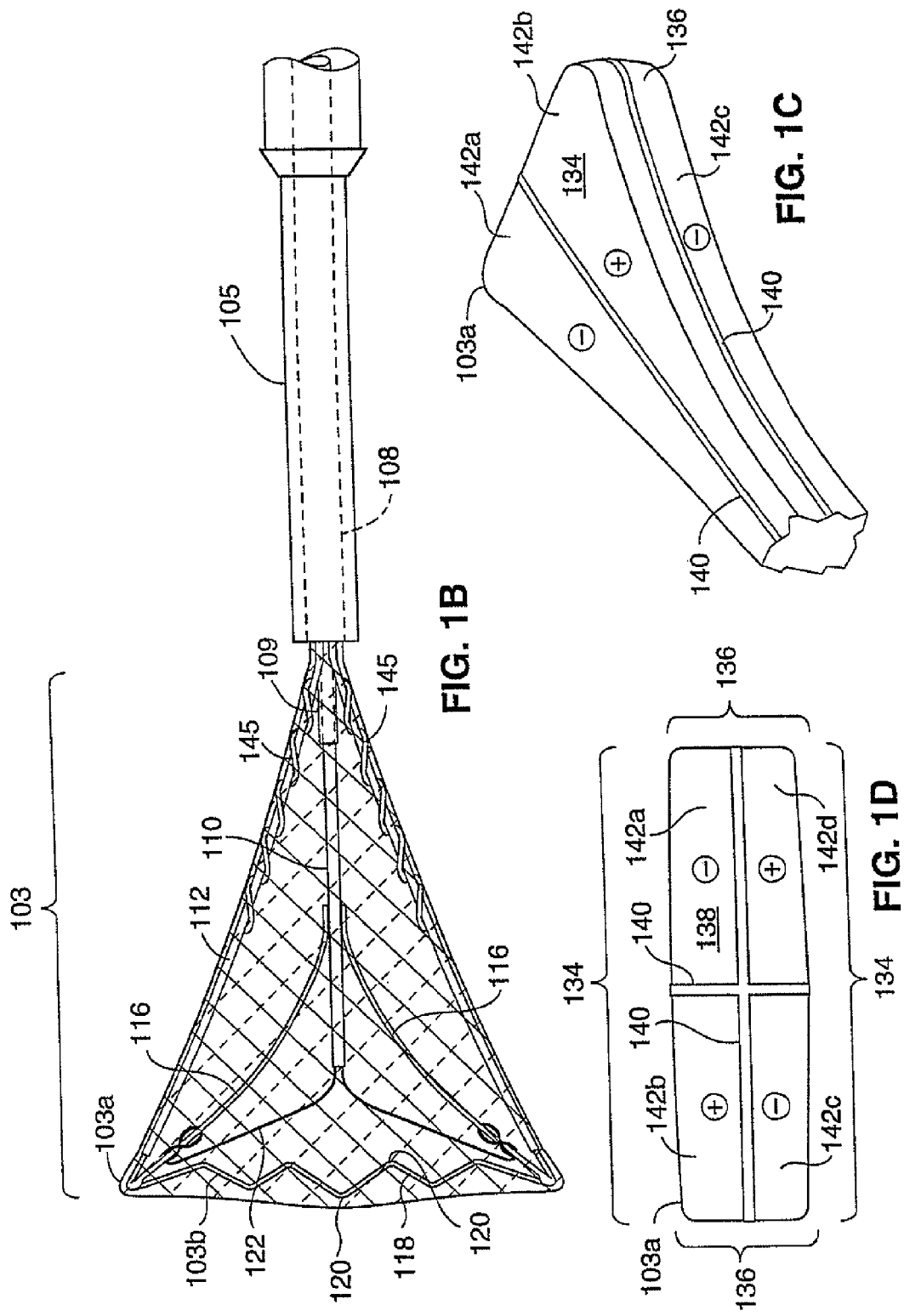

RADIO-FREQUENCY GENERATOR FOR POWERING AN ABLATION DEVICE

CLAIM OF PRIORITY

This application is a continuation of U.S. application Ser. No. 12/775,752 filed May 7, 2010, now abandoned, which is a divisional of U.S. application Ser. No. 11/211,016, filed Aug. 24, 2005, now issued as U.S. Pat. No. 7,717,909, which is a divisional of U.S. application Ser. No. 10/328,447, filed Dec. 23, 2002, now issued as U.S. Pat. No. 7,074,217, which a divisional of U.S. application Ser. No. 09/306,480, filed May 6, 1999, now issued as U.S. Pat. No. 6,508,815, which claims the benefit of Provisional Application 60/084,712, filed May 8, 1998, all of which are hereby incorporated herein by reference.

TECHNICAL FIELD OF THE INVENTION

The present invention relates generally to the ablation of tissue and more specifically to an apparatus and method for providing radio-frequency power to an ablation device.

BACKGROUND

Ablation of the interior lining of a body organ is a procedure which involves heating the organ lining to temperatures which destroy the cells of the lining or coagulate tissue proteins for hemostasis. Such a procedure may be performed as a treatment to one of many conditions, such as chronic bleeding of the endometrial layer of the uterus or abnormalities of the mucosal layer of the gallbladder. Existing methods for effecting ablation include circulation of heated fluid inside the organ (either directly or inside a balloon), laser treatment of the organ lining, and resistive heating using application of radio-frequency (RF) energy to the tissue to be ablated.

Techniques using RF energy provide an RF electrical signal to one or more electrodes in contact with the subject organ tissue. Electrical current flows from the electrodes and into the organ tissue. The current flow resistively heats the surrounding tissue. Eventually, the heating process destroys the cells surrounding the electrodes and thereby effectuates ablation.

Before the start of power delivery, blood and saline solution may surround the electrodes. As the cells surrounding the electrodes are destroyed, additional blood and saline solution will surround the electrodes. These conductive liquids act to decrease the electrode impedance. These liquids may be suctioned away during the ablation process. Absent these conductive liquids, the electrode impedance will increase with the destruction of the surrounding cells. Depending upon the specific electrode configuration, the impedance characteristics may change from as little as a fraction of an ohm to well over 200 ohms during the course of an ablation procedure.

The RF ablation technique must be performed using great care to prevent over-ablation. Monitoring of tissue surface temperature is normally carried out during these ablation procedures to ensure the temperature does not exceed 100° C. If the temperature exceeds 100° C., the fluid within the tissue begins to boil and to thereby produce steam. Because ablation is carried out within a closed cavity within the body, the steam cannot escape and may instead force itself deeply into the tissue, or it may pass into areas adjacent to the area intended to be ablated, causing embolism or unintended burning of adjacent tissues.

An RF ablation device must accurately determine the appropriate level of power. This power level must provide sufficient heating to effectuate ablation. At the same time, the power level must be controlled to prevent over-ablation. Moreover, an RF generator must be controlled to respond dynamically to changes in the impedance of the subject tissue.

Existing RF ablation devices generally apply power to electrodes having a relatively small surface area (e.g. forcept electrodes). Such electrodes ablate a relatively small surface area at a relatively high impedance. Accordingly, the required RF power is relatively low and simple to deliver (typically 80 Watts at approximately 100 Ohms). During an ablation procedure, the impedance characteristics of such electrodes may change. However, many generators are suitable for providing the relatively low power level over a range of high impedances.

To ablate a large tissue area with electrodes having a relatively small surface area, an operator must move electrodes about the tissue surface. This introduces a measure of imprecision. An electrode matched to the surface area of the subject tissue reduces this imprecision. However, matching the electrode area to the subject tissue area significantly increases the surface area of the electrode. Accordingly, the electrode requires significantly greater power levels to effect ablation. Moreover, relatively large surface areas are characterized by a relatively low initial impedance, which increases significantly during the course of an ablation.

It is therefore desirable to provide a power level sufficient to effectuate ablation on a relatively large surface area electrode. The power level, however, must not result in over-ablation. It is also desirable to dynamically control the RF generator to respond to impedance changes within the subject organ tissue. It is further desirable to provide an ablation method and device which allows the depth of ablation to be controlled reliably and which automatically discontinues ablation once the desired ablation depth has been reached.

BRIEF SUMMARY

An apparatus and method for use in performing ablation of organs and other tissues includes an RF generator configured to provide an RF signal to ablation electrodes. The power level of the RF signal is determined based on the subject area and depth of the volumetric ablation. The RF signal is coupled with the ablation electrode through a transformation circuit. The transformation circuit includes a low impedance and a high impedance transformation circuit. The low impedance and high impedance transformation circuits are selected based on the impedance of the ablation electrode in contact with the subject tissue. Vacuum level, impedance level, resistance level, and time are measured during ablation. If these parameters exceed determinable limits the ablation procedure is terminated.

BRIEF DESCRIPTION OF THE DRAWINGS

FIG. 1B is a top view of the distal end of the ablation device of FIG. 1A, shown with an applicator head in an extended position.

FIG. 1C is a perspective view of the applicator head in the extended position of FIG. 1B.

FIG. 1D is a front elevational view of the applicator head in the extended position of FIG. 1B.

DETAILED DESCRIPTION

Figure 1A:
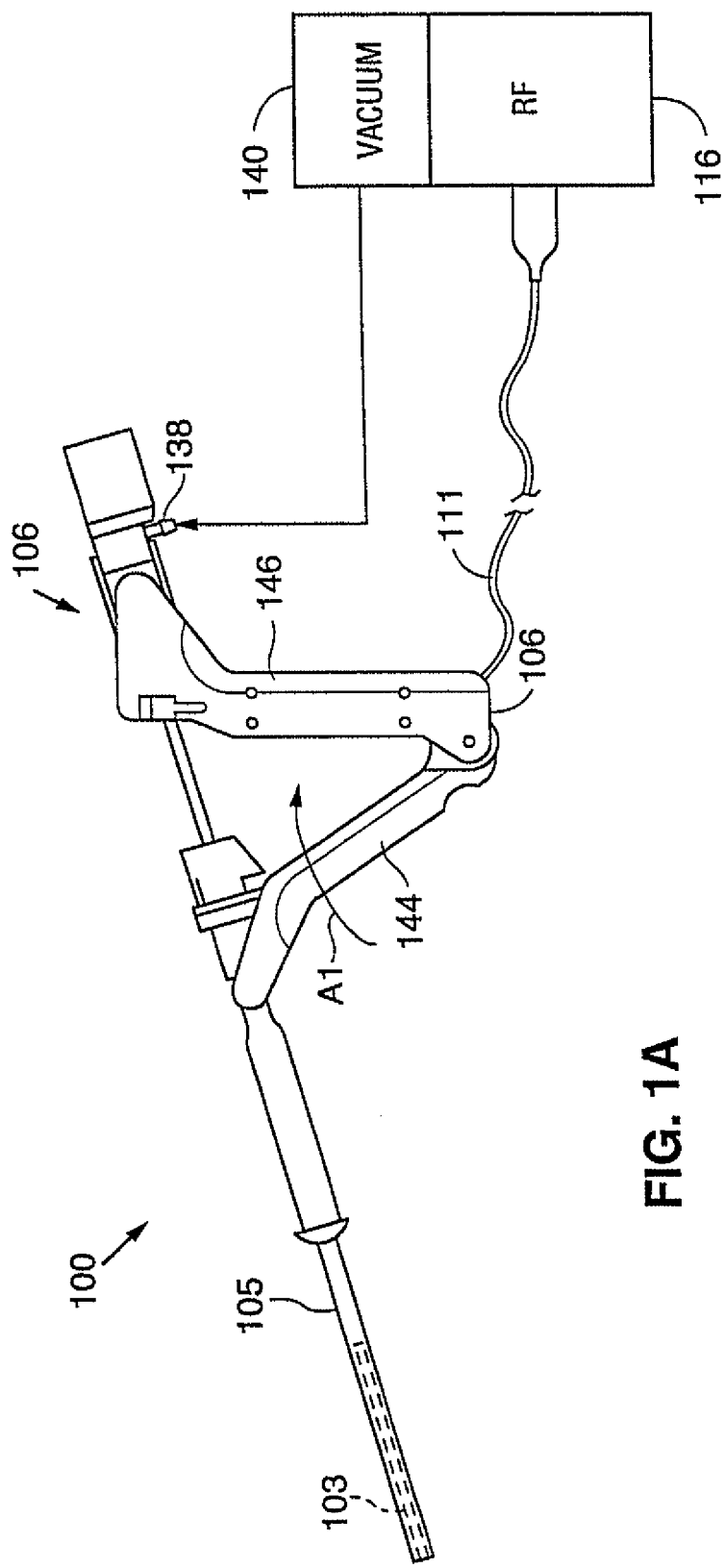
FIG. 1A is a side elevation view of an RF generator according to the invention and an ablation device suitable for use with the RF generator.

Referring to FIGS. 1A and 1B, an intrauterine ablation device 100 suitable for use with an RF generator 116 according to the present invention is comprised generally of three major components: an RF applicator head 103, a sheath 105, and a handle 106. The applicator head 103 is slidably disposed within the sheath 105 (FIG. 1A) during insertion of the device into the uterine cavity, and the handle 106 is subsequently manipulated as indicated by arrow A1 to cause the applicator head 103 to extend from the distal end of the sheath 105 (FIG. 1B).

Referring to FIG. 1B, applicator head 103 extends from the distal end of a length of tubing 108 which is slidably disposed within the sheath 105. Applicator 103 includes an external electrode array 103a and an internal deflecting mechanism 103b used to expand the array for positioning into contact with the tissue.

The RF electrode array 103a is formed of a stretchable metallized fabric mesh which is preferably knitted from a nylon and spandex knit plated with gold or other conductive material. Insulating regions 140 (FIGS. 1C, 1D) are formed on the applicator head to divide the mesh into electrode regions. The insulated regions 140 are preferably formed using etching techniques to remove the conductive metal from the mesh, although alternate methods may also be used, such as by knitting conductive and non-conductive materials together to form the array.

The array may be divided by the insulated regions 140 into a variety of electrode configurations. In a preferred configuration (FIG. 1C) the insulating regions 140 divide the applicator head into four electrodes 142a-142d by creating two electrodes on each of the broad faces 134. To create this four-electrode pattern, insulating regions 140 are placed longitudinally along each of the broad faces 134 as well as along the length of each of the faces 136, 138. The electrodes 142a-142d are used for ablation and, if desired, to measure tissue impedance during use.

Deflecting mechanism 103b and its deployment structure is enclosed within electrode array 103a. Referring to FIG. 1B, external hypotube 109 extends from tubing 108 and an internal hypotube 110 is slidably and co-axially disposed within hypotube 109. Flexures 112 extend from the tubing 108 on opposite sides of hypotube 109. A plurality of longitudinally spaced apertures (not shown) may be formed in each flexure 112. During use, these apertures allow moisture to pass through the flexures and to be drawn into exposed distal end of hypotube 109 using a vacuum source 140 fluidly coupled to hypotube 109 at vacuum port 138.

Internal flexures 116 extend laterally and longitudinally from the exterior surface of hypotube 110 and are each connected to a corresponding one of the flexures 112. A transverse ribbon 118 extends between the distal portions of the internal flexures 116. Transverse ribbon 118 is preferably pre-shaped such that when in the relaxed condition the ribbon assumes the corrugated configuration shown in FIG. 1B and such that when in a compressed condition it is folded along the plurality of creases 120 that extend along its length.

The deflecting mechanism 103b formed by the flexures 112, 116, and ribbon 118 shapes the array 103a into the substantially triangular shape shown in FIG. 1B, which is particularly adaptable to most uterine shapes. During use, distal and proximal grips 144, 146 forming handle 106 are squeezed towards one another to deploy the array. This action results in relative rearward motion of the hypotube 109 and relative forward motion of the hypotube 110. The relative motion between the hypotubes causes deflection in flexures 112, 116 which deploys and tensions the electrode array 103a.

Flexures 112, 116 and ribbon are preferably made from an insulated spring material such as heat treated 17-7 PH stainless steel. Each flexure 112 preferably includes conductive regions that are electrically coupled to the array for delivery of RF energy to the body tissue. Strands of thread 145 (which may be nylon) are preferably sewn through the array 103 and around the flexures 112 in order to prevent the conductive regions 132 from slipping out of alignment with the electrodes 142a-142d.

As will be discussed in detail below, the RF generator system according to the present invention utilizes an ablation power that is selected based on the surface area of the target ablation tissue. For uterine ablation, the RF power is calculated using the measured length and width of the uterus. These measurements may be made using conventional intrauterine measurement devices.

Alternatively, the ablation device 100 itself may be used to measure the uterine width by transducing the separation of flexures using a mechanical or electrical transducing means. Referring again to FIG. 1B, the ablation device 100 includes non-conductive (e.g. nylon) suturing threads 122 that extend between the hypotube 110 and the distal portion of the deflecting mechanism (FIG. 1B). Threads 122 are connected to an elongate wire (not shown) which extends through the tubing and is coupled to a mechanical transducer such as a rotatable bobbin (not shown) or an electrical transducer such as a strain gauge electrically coupled to an A/D converter to electrically transduce the separation distance of the flexures 112 and to electronically transmit the uterine width to a visual display and/or directly to the RF generator.

Figure 2:
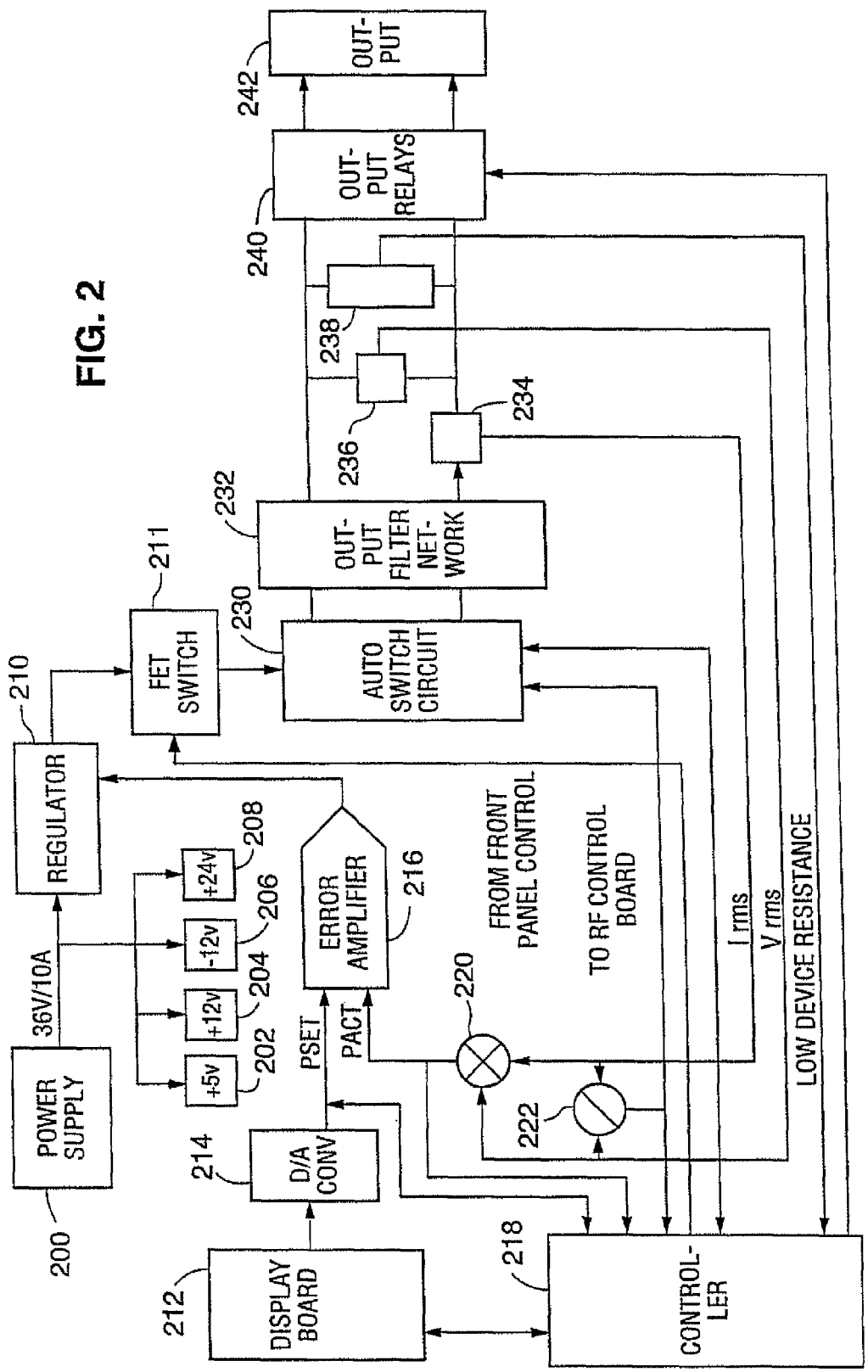
FIG. 2 is a circuit block diagram of the RF generator of FIG. 1.

Turning to FIG. 2, one preferred embodiment of an RF generator circuit is described. The circuit includes a power supply 200. The power supply 200 accepts an AC signal and generates a 36 volt DC signal at up to 10 amps. The power supply 200 connects to converters 202, 204, 206, and 208. The converters 202, 204, 206, and 208 generate +5, +12, −12, and +24 volt electric potentials, respectively. As needed, the converters 202, 204, 206, and 208 provide the electric potentials to various circuit components hereinafter described.

A display board 212 generally provides a user interface. This interface allows a user to input selection data and provides feedback information. The display board 212 provides a digital signal indicating a desired power setting to digital-to-analog (D/A) converter 214. The D/A converter 214 converts the incoming digital signal into a voltage potential. This voltage potential (PSET), representing the desired power setting, is provided to an error amplifier 216. The error amplifier 216 also receives a voltage potential representing the actual power (PACT) currently delivered to an ablation device. The error amplifier compares the set power signal to the actual power signal to determine whether output power should be increased or decreased. If the set power signal is greater than the actual power signal, the error amplifier 216 provides a positive signal to the regulator 210. In response, the regulator 210 increases the output power. If the set power signal is less than the actual power signal, the error amplifier 216 provides a negative signal to the regulator 210. In response, the regulator 210 decreases the output power.

The regulator 210 receives DC power from the power supply 200 and provides a RF signal to FET switch 211. The signal from the error amplifier 216 controls the pulse width modulation of the regulator 210. Pulse width increases effect an increase in power; pulse width decreases effect a decrease in power.

The FET switch 211 receives the RF signal from the regulator 210. The FET switch also receives a control signal from the controller 218. When energized, the control signal turns on the FET switch 211 so that the RF signal is provided to auto-switch circuit 230. When de-energized, the control signal turns off the FET switch 211 so that any signal provided by the regulator 210 is disconnected from the auto-switch circuit 230.

Figure 4:
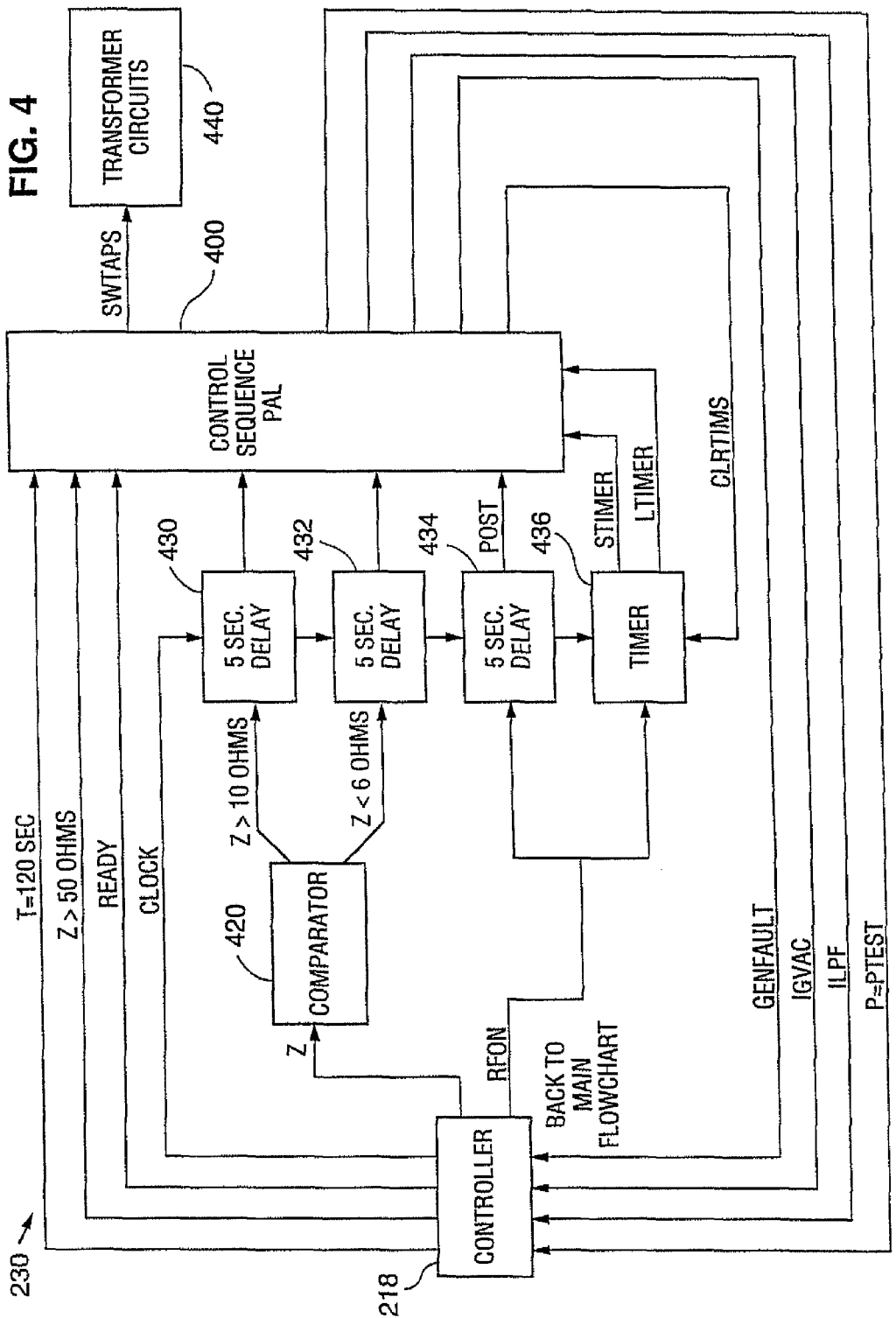
FIG. 4 is a circuit block diagram of the auto-switch circuit of FIG. 2, including additional circuit elements connected with the auto-switch circuit.

The auto-switch circuit 230 also receives control signals from the controller 218, and an impedance signal from the divider 222. Based on the control and impedance signals, the auto-switch circuit 230 selects between a low impedance and a high impedance transformation circuits 440 (FIG. 4). The output of the selected transformer circuit is provided to the filter network 232. The filter network 232 acts as a bandpass filter having a preferred center frequency of approximately 482 KHz. The filter network 232 reduces any higher-order harmonic signals on the RF signal. In addition, the filter network 232 decouples any DC components from the regulator 210.

Current detector 234 measures the current provided through the filter network 232. Similarly, the voltage detector 236 measures the voltage provided across the output of the filter network 232. These measured signals are provided to the divider 222 through RMS converters 221 and 222. The measured signals are also provided to the multiplier 220. The divider 222 divides the voltage signal by the current signal to produce a signal representing the effective impedance of an ablation device. The multiplier 220 multiplies the voltage signal by the current signal to produce a signal representing the actual power provided to an ablation device. As described above, the actual power signal is used by the error amplifier 216 to control the regulator 210. The effective impedance signal is used by the auto-switch circuit 230 to select between the low impedance and high impedance transformation circuit.

The actual power signal (PACT) from multiplier 220 and the effective impedance signal from divider 222 are both provided to the controller 218. The controller 218 also connects to the set power signal input of the error amplifier 116. The controller 218 is configured to measure the power set signal and to generate a set power signal. During an ablation procedure, if the controller 218 detects a terminal fault condition, the controller 218 drives the set power signal to zero and de-energizes the FET switch 211. Driving the set power signal to zero causes the regulator 210 to turn off the RF signal.

The RF generator also includes a DC resistance detector 238 connected across output relays 240. The DC resistance detector 238 measures the DC resistance of an external ablation device. The DC resistance detector 238 provides a signal related to this resistance to the controller 218. The controller uses this signal to detect a short circuit in an attached ablation device.

The output relays 240 receive the filtered RF signal from the filter network 232. The output relays 240 are configured to provide this signal to the output terminals 242 in response to a control signal from the controller 218. When energized, the output relays 240 connect the RF generator circuit to an ablation device through output terminals 242. When de-energized, the output relays 240 isolate the RF generator circuit from an ablation device.

Figure 3:
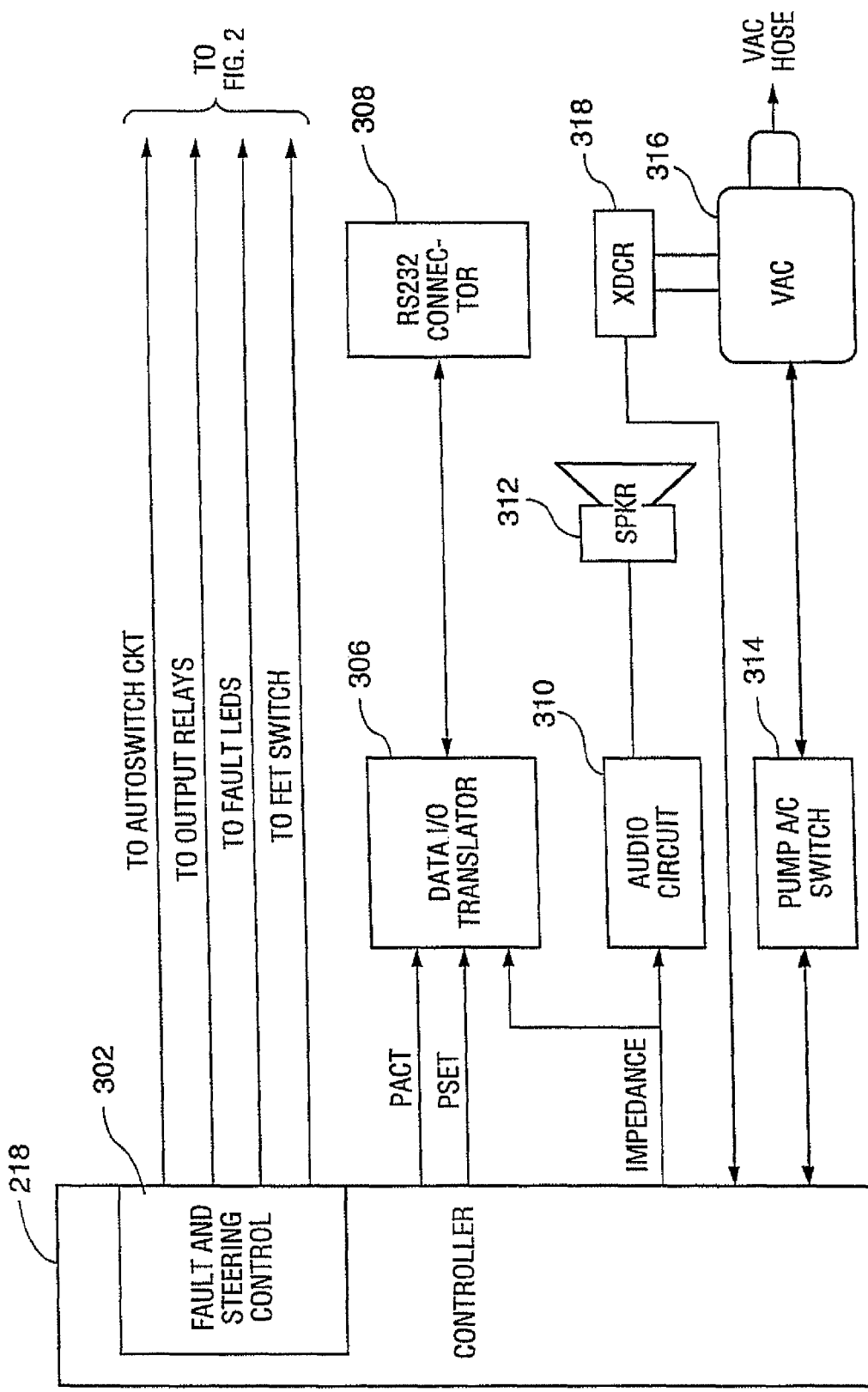
FIG. 3 is a circuit block diagram of the controller of FIG. 2, including additional circuit elements connected with the controller.

Turning to FIG. 3, a preferred embodiment of the controller 218 and additional related components are described. A fault and steering control block 302 of the controller 218 provides control signals to the display board 212, the FET switch 211, the auto-switch circuit 230, and the output relays 240.

The controller 218 provides the impedance signal from divider 222 (FIG. 2) to both an audio circuit 310 and a data I/O translator 306. The audio circuit 310 produces a frequency signal related to the impedance signal. Low impedances are transduced into higher frequency signals; high impedances are transduced into a lower frequency signals. The frequency signal lies within the range of audible frequencies and is used to drive a speaker 312. During the process of ablation, the measured impedance will increase. Accordingly, the frequency of the sound signal produced by the speaker 312 will decrease. This provides audible feedback of the ablation process to an operator. The audio circuit 310 may also be configured to provide signals that increase in frequency with increased impedance.

The controller 218 also provides the actual and set power signals and the vacuum signal to the data I/O translator 306. The data I/O translator converts these signals and the impedance signal into a related digital signal, which is provided over an RS232 connection 308.

Vacuum pump AC switch 314 is controlled by the controller 218. When activated, the pump AC switch connects AC power to a vacuum pump 316, which draws moisture from the ablation device and surrounding tissue. When deactivated, pump AC switch disconnects AC power from the vacuum pump 316. The vacuum pump 316 also includes a pressure transducer 318. The pressure transducer 318 is configured to measure the pressure induced within an ablation device. The pressure transducer 318 provides a signal representing this pressure to the controller 218, which monitors whether suction applied by the vacuum pump 316 is within determined limits.

Turning to FIG. 4, a preferred embodiment of the auto-switch circuit 230 is shown. The auto-switch circuit includes a control sequence PAL 400. The PAL 400 receives timer, impedance, and ready signals from controller 218. When activated, the timer signal indicates that the duration of the ablation has exceeded 120 seconds; the impedance signal indicates that the impedance of the ablation device exceeds 50 ohms; and the ready signal indicates that an operator has engaged an RF enable switch.

The impedance signal from the divider 222 (FIG. 2) is also provided to a comparator 420 via controller 218. If the impedance is greater than 10 ohms, the comparator 420 activates a signal to delay 430. If the impedance is less than 6 ohms, the comparator 420 activates a signal to delay 432. The delays 430 and 432 also receive a clock signal from controller 218. If either of the delays 430 or 432 continue to receive a signal from the comparators for more than five seconds, the respective delay activates a signal to the PAL 400. When the impedance is greater than 10 ohms for longer than five seconds, the PAL 400 provides a switch taps (SWTAPS) signal to the transformer circuit 440 selecting a high impedance transformation circuit. When the impedance is less than 6 ohms for longer than 5 seconds, the PAL selects a low impedance transformation circuit.

The controller 218 also provides an RF power on (RFON) signal to delay 434 and timer 436. If this signal remains active for greater than five seconds, delay 434 activates a power on self test (POST) signal to PAL 400. In addition to the RFON signal, timer 436 also receives a clear timer (CLRTMS) signal from the PAL 400. The CLRTMS signal is activated upon a change of state in the SWTAPS signal and indicates that the transformer circuit has changed to match the impedance of the ablation device. Upon receiving either the RFON or the SWTAPS signal, the timer 436 resets a short and a long timer. After expiration of the short timer, the timer 436 activates the short timer signal, which is provided to the PAL 400. After expiration of the long timer, the timer 436 activates the long timer, which is also provided to PAL 400. These signals are used by the PAL 400 to generate condition signals. The condition signals are used in conjunction with fault signals to determine whether to terminate an ablation procedure.

The transformation circuit 440 is connected between the FET switch 211 and the output filter network 232 (FIG. 2). The transformation circuit 440 operates to match the impedance of the regulator 210 to that of an ablation device. Again, the impedance of an ablation electrode in contact with the subject tissue may change significantly during the course of an ablation. By matching the impedance of regulator 210 to that of the electrode, the regulator 210 is able to deliver a relatively constant power level. This in turn allows accurate and uniform ablation.

Alternatively, if the impedance of a regulator were matched to a low electrode impedance then the regulator's power delivery will decline as the electrode impedance increases. If the impedance of the regulator were instead matched to a high electrode impedance then at a low initial electrode impedance the regulator will bear a high current load. This load may cause damage or heating to regulator components.

Accordingly, the transformation circuit 440 include a low impedance transformation circuit and a high impedance transformation circuit. A preferred low impedance transformation circuit matches the impedance of the regulator 210 to a three ohm load. A preferred high impedance transformation circuit matches the impedance of the regulator 210 to a twenty-five ohm load. These transformation circuits allow a regulator to provide relatively constant power delivery.

Again, the PAL 400 provides condition signals to the controller 218. Specifically, the PAL 400 generates a GENFAULT, an IGVAC, an ILPF and a PTEST signal. The GENFAULT signal indicates that the PAL has detected a fault condition and that the ablation should be terminated. The IGVAC signal indicates that the vacuum circuit has just been energized. Accordingly, any vacuum faults should be ignored for 2 seconds while the vacuum pump establishes the appropriate pressure. The IPLF signal indicates that any low priority faults should be ignored. The IPLF signal is activated during start up so that non-critical transient faults do not terminate the ablation procedure. The PTEST indicates that a low-level RF signal is currently being applied to the transformation circuit. The low-level RF signal is used to measure RF impedance before applying full power.

Figure 5:
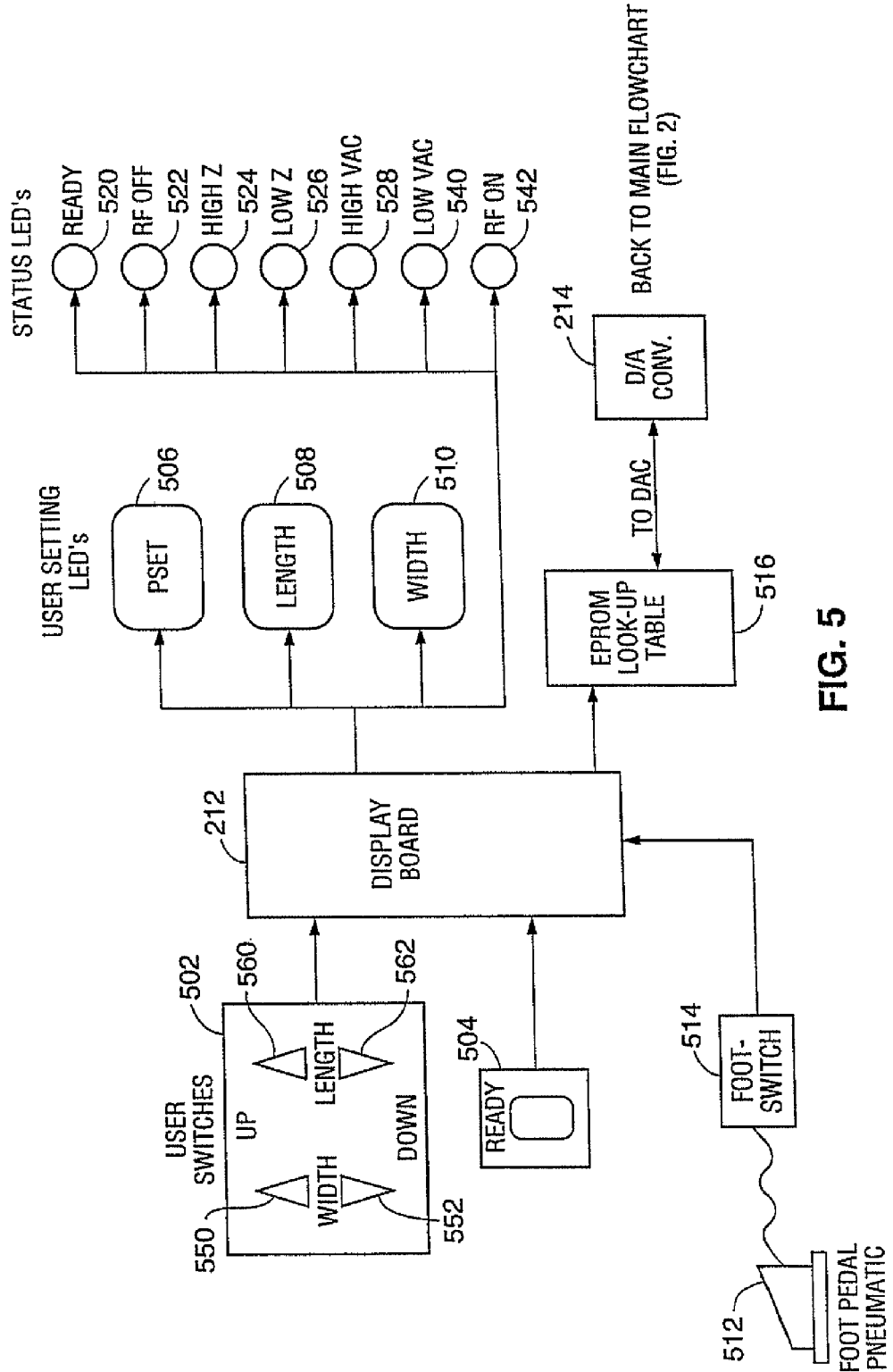
FIG. 5 is a circuit block diagram of the display board of FIG. 2, including additional circuit elements connected with the display board.

Turning to FIG. 5, the display board 212 of FIG. 2 and additional related components are described. The display board 212 connects to length and width selection switches 502. After determining the length and width of a subject uterine cavity, an operator enters the appropriate settings using switches 502. The length and width selections are shown on displays 508 and 510, respectively. To increase the width, an operator engages the up arrow switch 550. To decreases the width, an operator engages the down arrow switch 552. To increase the length, an operator engages the up arrow switch 560. To decrease the length, an operator engages the down arrow switch 562. A signal indicating the length and width are provided to the EPROM 516. The EPROM 516 converts the length and width to a set power level according to the following relationship:

$$P = L \times W \times 5.5$$

Where P is the power level in Watts, L is the length in centimeters, W is the width in centimeters, and 5.5 is a constant having units of Watts per square centimeter.

The display board 212 also provides a signal to a set power display 506. This signal is determined based on the length and width selections so that the set power display 506 shows the current power setting.

After an operator selects an appropriate length and width setting, he or she engages the ready switch 504. The ready switch 504 provides a signal to the display board 212, which is in turn provided to the controller 218. The ready switch 504 indicates that the operator is ready to begin an ablation procedure.

After an operator engages the ready switch 504, the operator may then depress foot pedal 512. The foot pedal 512 connects to foot switch 514 to provide a signal to the display board 212, which is also provided to the controller 218. This signal indicates that the RF generator should apply RF power to an ablation device.

The display board 212 also connects to status LED's including a READY 320, RF OFF 322, HIGH Z 324, LOW Z 326, HIGH VAC 328, LOW VAC 340, and RF ON 342. The display board 212 controls these LED's based on signals received from the controller 218 and from the user inputs.

The READY LED 520 indicates that the RF generator is in a ready condition, and that activation of the foot switch 514 would activate RF power. The RF OFF LED 522 indicates that a DC short condition exists with the ablation device currently connected to the RF generator and that the RF generator is not currently providing power to an ablation device. The HIGH Z LED 524 indicates that the impedance exceeds a determined level. When this condition occurs, the controller automatically terminates ablation. The LOW Z LED 526 indicates that the impedance falls below a determined level. When this condition occurs, an RF short condition exists. The HIGH VAC LED 528 indicates that the vacuum pump 140 is currently exceeding determined acceptable vacuum levels. For example, this condition may be generated by an operator standing on the suction tubes connecting the vacuum pump 140 to port 138. The LOW VAC LED 540 indicates that the vacuum pump 140 is currently below an acceptable vacuum level. For example, this condition may be generated if the vacuum pump 140 were not properly attached to port 138. The RF ON LED 542 indicates that the RF generator is currently providing power to an ablation device.

Figure 6:
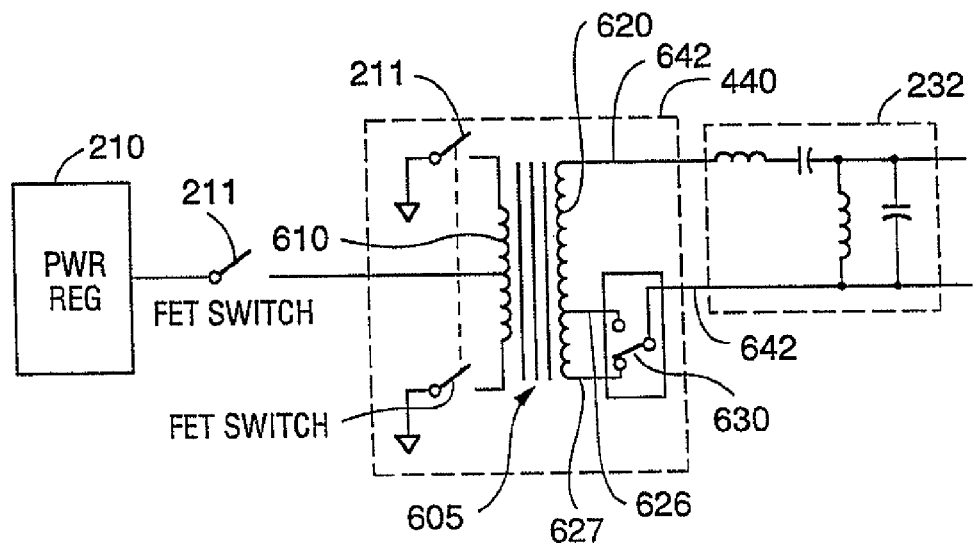
FIG. 6 is a circuit diagram of one preferred embodiment of the transformer circuit of FIG. 5 connected with a regulator and a filter network.

Turning to FIG. 6, a preferred embodiment of a regulator 210, FET switch 211, transformation circuit 440, and output filter network 230 are shown. The transformation circuit 440 includes a transformer 605 having a power winding 610 and a load winding 620. The power winding 610 connects to FET switch 211 for receiving RF power from the regulator 210. The load winding 620 is electromagnetically coupled with power winding 610. Accordingly, electric power provided to the power winding 610 is transferred to the load winding 620.

The load winding 620 includes a center tap 626 which divides the load winding into a first portion 622 and a second portion 624. Switch 630 selects between the center tap 626 and an exterior tap 627. Selection of the center tap 626 provides a circuit matched to a lower impedance. Selection of the exterior tap 627 provides a circuit matched to a higher impedance. Alternatively stated, the switch 630 selects the transformation ratio between the power winding 610 and the output terminals 642. The output terminals 642 connect to an output filter network 232 having the above described bandpass characteristics.

Figure 7:
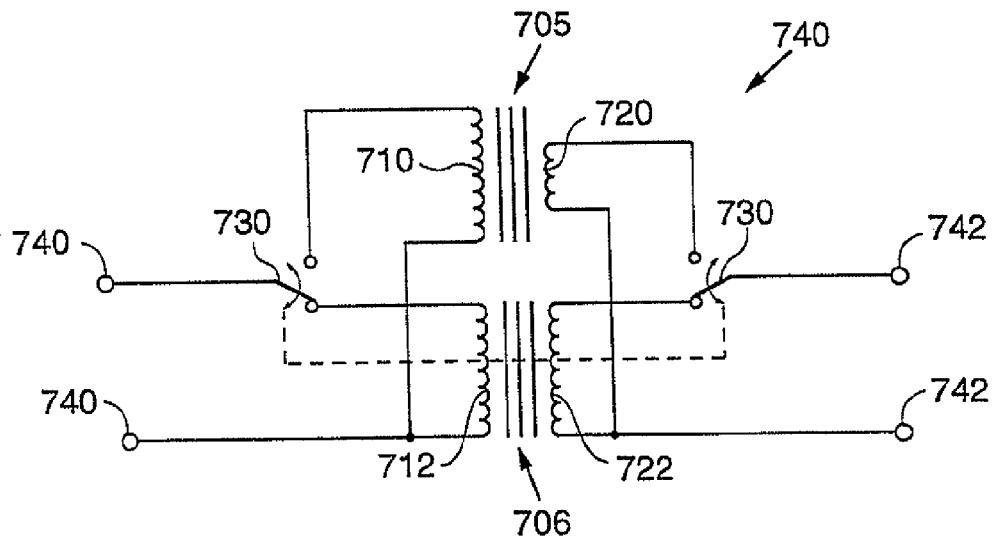
FIG. 7 is a circuit diagram of another embodiment of the transformer circuit of FIG. 5.

Turning to FIG. 7, an alternative embodiment of a transformation circuit is shown. The transformation circuit 740 includes a first transformer 705 having a power winding 710 and a load winding 720. The transformer switch circuit also includes a second transformer 706 having a power winding 712 and a load winding 722. The transformation ratio of the first transformer 705 is matched to a low impedance. The transformation ratio of the second transformer 706 is matched to a high impedance.

Switch 730 is connected to select between the first transformer 705 and the second transformer 706. As shown, the switch 730 selects the first transformer 705 to electrically couple input terminals 740 to output terminals 742. The switch may also select the second transformer 706 to electrically couple input terminals 740 to output terminals 742.

Figure 8:
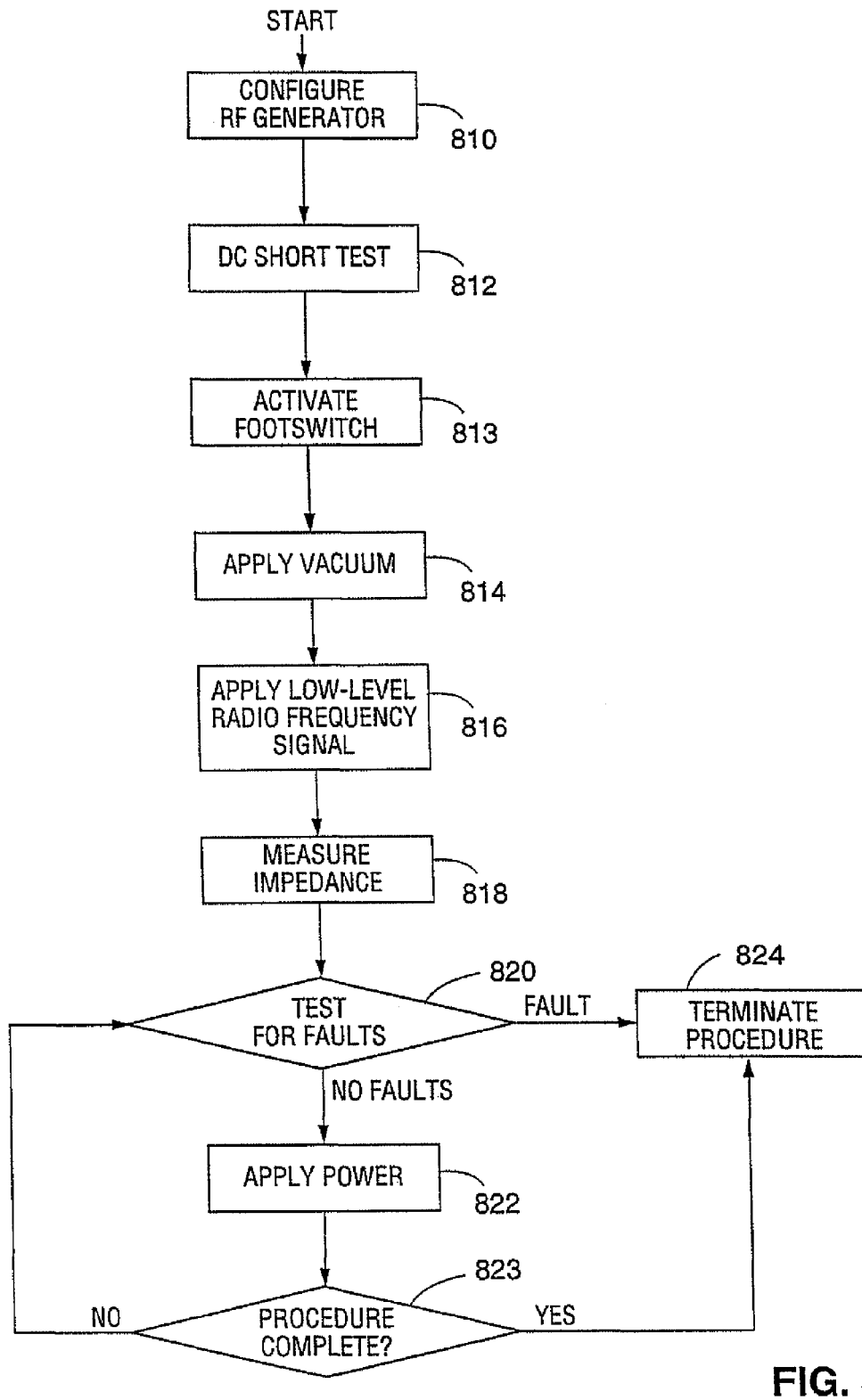
FIG. 8 is a flow chart showing the operation of an RF generator according to the invention.

Turning to FIG. 8, a flow chart showing the preferred operation of an RF generator used to power an ablation device is illustrated. At block 810, an operator selects a length and width related to the size of the subject uterus and activates a ready switch.

At block 812, the RF generator measures DC resistance through the ablation device. A measured resistance below 200 ohms indicates a short circuit. If a short circuit is detected, the RF generator will provide an indication to the operator and terminate the procedure. A measured resistance greater than 200 ohms indicates acceptable contact of the ablation device with the subject uterus. At block 811, the operator may then activate a foot-switch to apply power to an RF regulator.

At block 814, the RF generator applies power to a vacuum pump. After a few seconds, the pressure within the subject uterus will drop.

At block 816, the RF generator applies a low-level RF signal (e.g. between 5 and 10 Watts) to the ablation device. At block 820, the RF generator tests for faults which indicate that the procedure should be terminated. Specifically, the RF generator continues to test the DC resistance. The RF generator also tests whether the RF impedance falls within acceptable limits (e.g. 0.5-50 ohms), and whether the vacuum level falls within acceptable limits. During the first few seconds (e.g. 2 seconds) these faults may be ignored, as the transient characteristics may exceed fault tolerances.

If the RF generator does not detect any faults, it proceeds to block 822. Here, the RF generator applies full power to the ablation device. At the beginning of the ablation procedure, the power level may be gradually increased to the full power setting. At block 823, the RF generator tests whether the impedance of the subject uterus has exceeded fifty ohms or if the duration of the ablation has exceeded 120 seconds. If ether of these events occur, the ablation is complete and the procedure is terminated at block 824. Otherwise, the RF generator continues to test for faults at block 820. Upon detection of a fault the procedure is similarly terminated and power to the ablation device is disabled.

Figure 9:
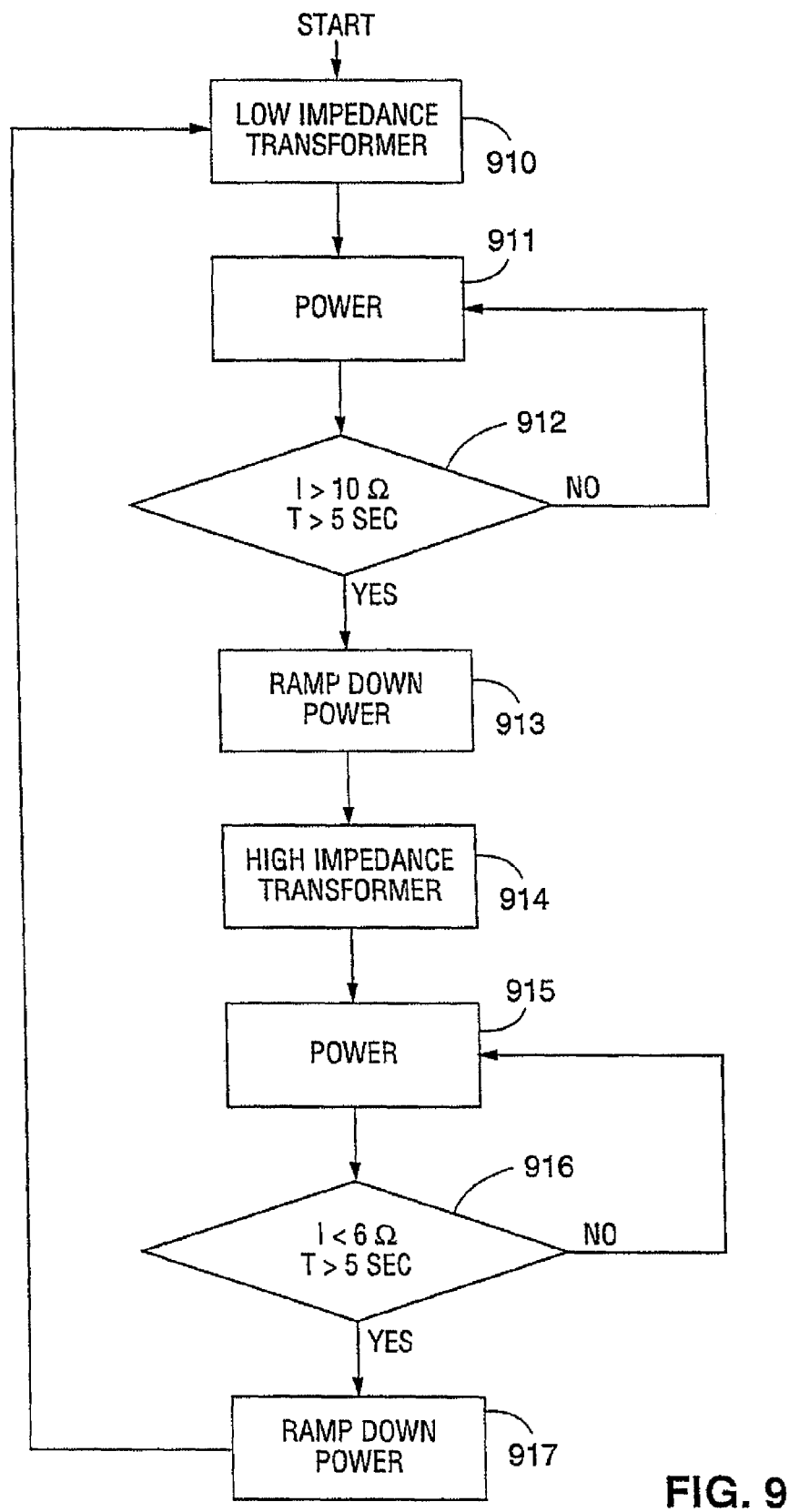
FIG. 9 is a flow chart showing the operation of an the auto-switch circuit according to the invention.

The process of applying power as shown at block 822 will now be discussed in greater detail. Turning to FIG. 9, a flow chart showing the preferred operation of the application of power through a transformation circuit is illustrated. The transformation circuit is used to couple power supplied by the RF generator to an ablation device. As described above, a preferred transformation circuit includes a low impedance transformation circuit and a high impedance transformation circuit. The operation of the transformation circuit begins at block 910, where the low impedance transformation circuit is selected. At block 911, a low level RF signal is applied to the transformation circuit.

At block 912, the impedance of an ablation device is measured. If the impedance has not exceeded 10 ohms for 5 seconds the process returns to block 911. Here, the pulse width of the RF signal will increase until it reaches the selected power level. Upon reaching the selected level, the pulse width is controlled according to changes in the electrode impedance to maintain a constant power level.

The process again returns to block 912 where the impedance of the ablation device is again measured. In the preferred embodiment, if the impedance exceeds 10 ohms for 5 seconds, the process proceeds to block 913. Here, the pulse width of the RF signal must be decreased so that the transformation circuit may switch from the low impedance transformation circuit to the high impedance transformation circuit.

At block 914, after reducing the RF signal to a low level, the switch changes states to select the high impedance transformation circuit. At block 915, power is then ramped back up to the selected level. This reduction in power and gradual increase reduces transient spikes which might result from the switching between the low impedance transformation circuit and the high impedance transformation circuit.

At block 916, the impedance of the ablation device is measured. If the impedance has not dropped below 6 ohms for 5 seconds, the process returns to block 915. Here, the pulse width is controlled to deliver the selected power level.

The process again returns to block 916 where the impedance of the ablation device is again measured. In the preferred embodiment, if the impedance drops below 6 ohms for 5 seconds, the process proceeds to block 917. Here, the pulse width of the RF signal must be decreased so that the transformation circuit may switch from the high impedance transformation circuit to the low impedance transformation circuit at block 910. The operation of the transformation circuit continues in this manner until the ablation is terminated. At termination, the power is turned off and the RF generator is disconnected from the ablation device.

Although the forgoing description is with reference to the ablation of a uterus, the present invention is applicable to the ablation of other body tissues. In addition, although the RF generator is described with reference to a particular circuit many other configurations are suitable for implementing the teachings of the invention. Those having ordinary skill in the art will certainly understand from the embodiments disclosed herein that many modifications are possible without departing from the teachings hereof. All such modifications are intended to be encompassed within the following claims.

What is claimed is:

1. A system for ablating tissue comprising:
   an RF ablation device, wherein the RF ablation device is configured to transition from a compressed condition to a relaxed condition, and wherein the RF ablation device is configured to automatically transmit dimensional data to the RF generator; and
   an RF generator coupled to the RF ablation device, wherein the RF generator is configured to receive the dimensional data corresponding to tissue to be ablated, and wherein the RF generator is configured to automatically select an RF power based on the dimensional data, and wherein the RF generator is configured to provide an RF signal at the selected RF power to the RF ablation device.

2. The system of claim 1 further comprising:
a DC resistance detector for measuring a DC resistance of the RF ablation device.

3. The system of claim 1 wherein the RF generator is configured to test an RF impedance of the tissue.

4. A system for ablating tissue comprising:
an RF ablation device, wherein the RF ablation device includes an applicator head comprising a plurality of flexures, wherein the RF ablation device is configured to cause the plurality of flexures to transition from a compressed condition to a relaxed condition, and wherein the RF ablation device is configured to determine the dimensional data by transducing a distance of separation of two of the flexures when in the relaxed condition;
an RF generator coupled to the RF ablation device, wherein the RF generator is configured to receive the dimensional data corresponding to tissue to be ablated, and wherein the RF generator is configured to automatically select an RF power based on the dimensional data, and wherein the RF generator is configured to provide an RF signal at the selected RF power to the RF ablation device.

5. A system for ablating tissue comprising:
an RF ablation device, wherein the RF ablation device includes an expandable applicator head configured to be positioned in a uterine cavity, and wherein the RF ablation device is configured to cause the applicator head to transition from a compressed condition to a relaxed condition, and wherein the RF ablation device is configured to determine data related to the uterine cavity based on a degree of expansion of the applicator head when in the relaxed condition; and
an RF generator coupled to the RF ablation device, wherein the RF generator is configured to receive the data corresponding to tissue to be ablated, and wherein the RF generator is configured to automatically select an RF power based on the data, and wherein the RF generator is configured to provide an RF signal at the selected RF power to the RF ablation device.

6. The system of claim 5 wherein the data includes an impedance of the ablation device.

7. The system of claim 5 wherein the RF generator provides a relatively constant power.

8. The system of claim 5 wherein the RF ablation device includes an inner hypotube and an outer hypotube, and wherein the inner hypotube is slidably and coaxially disposed within the outer hypotube, and wherein relative motion between the inner hypotube and the outer hypotube causes the expandable applicator head to expand.

9. The system of claim 5 wherein the RF ablation device includes an indicator mechanism operatively coupled to the applicator head to indicate the degree of expansion of the applicator head.

10. The system of claim 9 wherein the indicator mechanism is mechanically operatively coupled to the applicator head.

11. The system of claim 9 wherein the indicator mechanism is electrically operatively coupled to the applicator head.

12. The system of claim 9 wherein the indicator mechanism indicates the degree of expansion of the applicator head based on a relative axial location of the inner hypotube and the outer hypotube.

13. The system of claim 5 wherein the RF generator is configured to automatically receive the data corresponding to the tissue to be ablated.

14. The system of claim 5 wherein the expandable applicator head includes an internal frame configured to move the applicator head from a non-expanded shape to an expanded shape.

15. The system of claim 14 wherein the RF ablation device includes a sensor configured to sense a degree of expansion of the applicator head, and wherein the sensor is configured sense movement of the internal frame.

16. The system of claim 5 wherein the RF ablation device includes a sensor for sensing a degree of expansion of the applicator head.

17. The system of claim 5 wherein the RF ablation device is configured to electrically transmit the data to the RF generator.

18. The system of claim 5 wherein the RF ablation device is configured to electrically transmit the data to a visual display.

19. The system of claim 5 wherein the data includes a width of the uterine cavity.

* * * * *